United States Patent [19]

Häfele et al.

[11] Patent Number: 5,279,855
[45] Date of Patent: Jan. 18, 1994

[54] MANUFACTURE OF INERT, CATALYTIC OR GAS-SENSITIVE CERAMIC LAYERS FOR GAS SENSORS

[75] Inventors: Edelbert Häfele, Karlsruhe; Karl-Heinz Hardtl, Hagenbach; Andreas Müller, Heidelberg; Ulrich Schönauer, Karlsruhe, all of Fed. Rep. of Germany

[73] Assignee: ROTH-Tecknik GmbH & Co. Forschung für Automobil und Umwelttechnik, Gaggenau, Fed. Rep. of Germany

[21] Appl. No.: 726,152
[22] PCT Filed: Jul. 7, 1988
[86] PCT No.: PCT/DE88/00419
  § 371 Date: Sep. 28, 1989
  § 102(e) Date: Sep. 28, 1989
[87] PCT Pub. No.: WO89/00687
  PCT Pub. Date: Jan. 26, 1989

Related U.S. Application Data

[63] Continuation of Ser. No. 423,424, Sep. 28, 1989, abandoned.

[30] Foreign Application Priority Data

Jul. 11, 1987 [DE] Fed. Rep. of Germany ....... 3723052

[51] Int. Cl.$^5$ .................. B05D 3/02; G01N 27/12
[52] U.S. Cl. .................. 427/226; 427/282; 427/419.3; 427/126.3; 338/34
[58] Field of Search ............. 427/226, 282, 419.3, 427/126.3; 73/23.2, 31.06; 338/34, 35; 502/525

[56] References Cited

U.S. PATENT DOCUMENTS

| | | | |
|---|---|---|---|
| 3,900,815 | 8/1975 | Taguchi | 338/34 |
| 3,929,609 | 12/1975 | Gray et al. | 338/34 |
| 3,951,603 | 4/1976 | Obayashi et al. | 23/232 E |
| 4,392,180 | 7/1983 | Nair | 361/321 |
| 4,507,643 | 3/1985 | Sunano et al. | 338/34 |
| 4,692,429 | 9/1987 | Sekido et al. | 502/303 |

FOREIGN PATENT DOCUMENTS

| | | |
|---|---|---|
| 881051 | 5/1980 | Belgium . |
| 2908916 | 9/1986 | Fed. Rep. of Germany . |
| 3606500 | 9/1987 | Fed. Rep. of Germany . |
| 58-99741 | 9/1983 | Japan . |

OTHER PUBLICATIONS

"Patent Abstract of Japan" vol. 7, No. 18 (P-170) [1163] Jan. 25, 1983.

Primary Examiner—Roy King
Attorney, Agent, or Firm—Spencer, Frank & Schneider

[57] ABSTRACT

The invention concerns a process for manufacturing inert, catalytic or gas-sensitve ceramic layers for gas sensors which comprises coating an uncoated insulative substrate with a layer of paste composed of a powdered semiconductor material of SrTiO$_3$ and an organic paste material having a thickness of 1 to 100 um and then subjecting the coated substrate to a three phase thermal treatment.

8 Claims, 2 Drawing Sheets

MANUFACTURE OF INERT, CATALYTIC OR GAS-SENSITIVE CERAMIC LAYERS FOR GAS SENSORS

This application is a continuation application Ser. No. 07/423,424, filed Sep. 28th, 1989, now abandoned.

BACKGROUND OF THE INVENTION

1. Field of the Invention

The invention relates to a method of producing inert, catalytically active or gas sensitive ceramic layers for gas sensors, particularly for potentiometric or resistive gas sensors, preferably with a volume effect, such ceramic layers being produced from a paste composed of a powdered basic ceramic material and an organic basic material for the paste.

1'. Technology Review

The concentration of gases, particularly the concentration of oxygen and reducing gases, is measured to an increasing degree by means of suitable sensors. Perovskite, particularly mixed titanium oxides, among others, have been employed as semiconductors for such sensors. In dependence on the partial pressure of the gases to be measured and the sensor temperature, these semiconductors exhibit a great change in electrical resistance. If the temperature is known or is compensated, it is possible to utilize the measurement of the semiconductor resistance to determine the partial pressure of these gases to be measured.

Such sensors can be miniaturized and are extremely resistant to external influences because of the chemical stability and mechanical hardness of the semiconductor ceramics active in the measurements and are therefore almost ideally suited for measuring tasks in difficultly accessible, rough environments.

A particular requirement for gas sensors has developed in the automobile industry because, for reasons of environmental protection, it is necessary to set the fuel-/air mixture in every driving state as accurately as possible. However, in this connection the requirements to be met by the sensors are especially high; particularly for use in high revolution internal-combustion engines involving up to 6000 rpm the response time of the sensors must be extremely short.

Semiconductors for gas sensors are presently produced by three different methods:
1. in a thin-film process;
2. by sintering of ceramic pellets;
3. by manually applying the paste with the aid of a brush.

The production of semiconductors for gas sensors in a thin-film process by way of reactive high frequency sputtering is disclosed, for example, in European Patent No. 0,131,731.

This method makes it possible to produce extremely thin gas sensors having a very small surface area.

Sensors produced according to this method exhibit a very "fast" response behavior, i.e. the change in resistance takes place with a very short time delay compared to the change in concentration of the gas being measured.

However, this manufacturing method is very complicated and thus expensive because it must be performed in a high vacuum and because the sputtered-on mixed oxide layers must be subjected to further treatment.

Due to the short free path lengths of the particles to be applied during sputtering and the resulting collision processes, no exact geometric structures can be produced even if templates are employed.

Moreover, doping the semiconductors in order to optimize their characteristics is possible only very conditionally since the number of elements that can be applied simultaneously by sputtering is limited. For these reasons, the thin-film technology is acceptable only in very specific fields.

Many sensors are therefore produced as ceramics by way of sintering. Such sintered sensors are disclosed, for example, in U.S. Pat. Nos. 4,044,601, 3,953,173 and 4,454,494.

The thickness of the sintered ceramic layer is at least 20 $\mu$m, usually, however, 500 $\mu$m. The speed of response of such sensors is noticeably poorer compared to those produced in a thin-film process (sputtering) because the time required to respond to changes in the concentration of the gas being measured is proportional to the square of the layer thickness and therefore increases considerably with increasing layer thickness.

DE-OS 3,024,449 discloses that semiconductors for gas sensors can be produced by manually applying a paste containing the semiconductor material. The layers are then more than 20 $\mu$m thick. The method is difficult to reproduce, requires subsequent treatment and is not suitable for the mass production of gas sensors.

For measuring technology reasons it may be of advantage to coat the gas sensitive semiconductor layer with a chemically inert, not gas sensitive intermediate layer and a catalytically active layer thereabove.

SUMMARY

It is therefore the object of the present invention to provide a reproducible, simple, cost-effective method suitable for the mass production of inert, catalytically active or gas sensitive ceramic layers for gas sensors with which ceramic semiconductors can be produced with a layer thickness of less than 100 $\mu$m, preferably less than 20 $\mu$m and a correspondingly fast response speed, with such ceramic layers being covered by an inert or a catalytically active layer, if required.

This method is intended to permit the production of miniaturized gas sensors. The semiconductors are to be producible in special, given geometric shapes with sharply defined edge zones.

DETAILED DESCRIPTION OF THE INVENTION

This is accomplished by the invention in that (a) a substrate is coated with the paste by screen printing;

(b) a layer thickness of 1 to 100 $\mu$m, preferably 1 to 20 $\mu$m, is maintained;

(c) the coated substrate is subjected to a thermal treatment such that, in a first heating phase at a temperature, for example, of about 150° C., the liquid components of the organic paste base material are evaporated, in a second heating phase at a temperature, for example, of about 350° C., the solid components of the organic paste base material residue are combusted freely and this is followed by a third heating phase at a temperature, for example, of about 1,330° C., the duration and maximum temperature of which are selected in such a manner that separation of the basic semiconductor material from the substrate is prevented.

Figure 2:
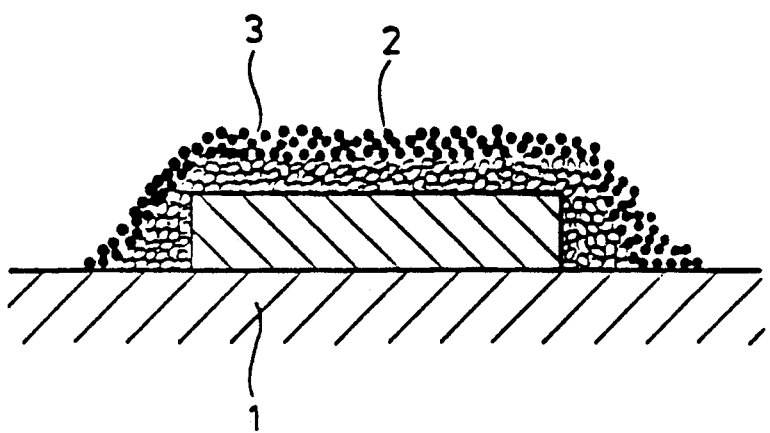
FIG. 2 illustrates an inert, catalytic or gas-sensitive ceramic layer in cross-section, including a substrate (1), an inert layer (2), and a catalytically active layer (3).

The substrate 1 may here be composed of a chemically inert, high temperature resistant electrical insulator. However, the manufacturing process may also be repeated in which case the substrate is then an already coated substrate onto which first an inert layer 2 and then a catalytically active layer 3 or a further gas sensitive semiconductor layer are applied (FIG. 2).

The screen printing technique is generally known as a color printing method for printing on paper and cloth. However, in the past it has not yet been employed for the production of gas sensors.

Gas sensors produced by screen printing can be manufactured economically because the time and energy consuming sintering step and the sputtering in a high vacuum required for the thin film process as well as the subsequent treatment necessary in both cases are eliminated.

The semiconductor material can be produced in layer thicknesses down to the order of magnitude of 1 $\mu$m. Thus, gas sensors result which have a high response speed (FIG. 2). Moreover, the geometric shape of the semiconductor can be easily adapted to its location of use and to the conditions of use, with it being possible to miniaturize the sensor—in contrast to the sintering technique. A particular advantage is that further gas sensitive or inert or catalytically active layers can be applied onto the gas sensitive layer in the same process.

Therefore screen-printing is particularly suitable for the production of large numbers of sensors.

All materials that are sufficiently chemically stable under the conditions under which the gas sensor is employed (300° to 1200° C.) and do not interact with the active measuring layer are suitable as substrates.

EXAMPLES

Figure 1:
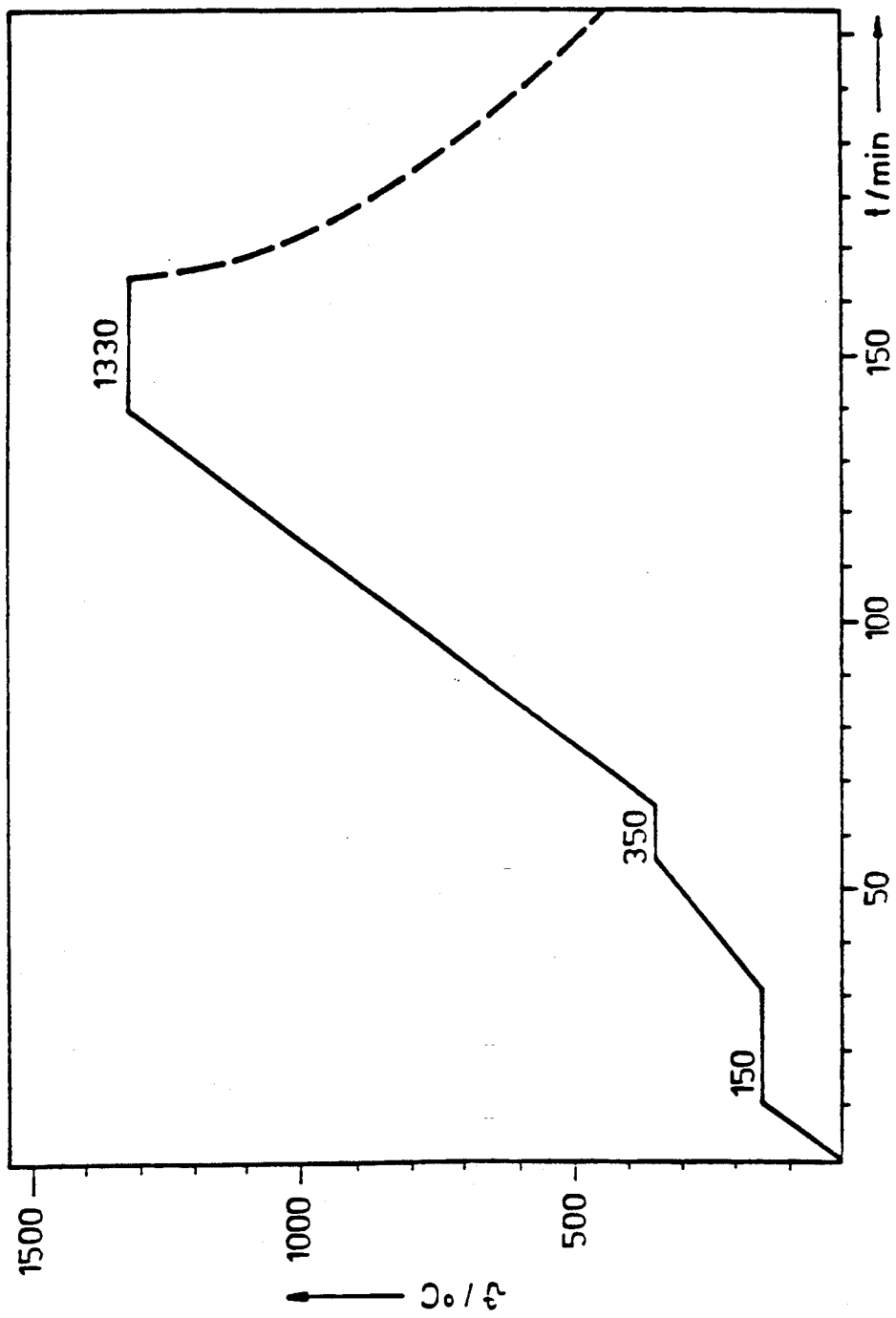
FIG. 1 illustrates a three-state thermal treatment useful in the production of inert, catalytic or gas-sensitive ceramic layers for gas sensors including a first heating phase at 150° C. to evaporate liquid components, a second heating phase at 350° C. to combust organic residue, and a third heating phase at 1,330° C.

The invention will now be described in greater detail with reference to an example thereof:

Production of the paste from 70% SrTiO$_3$ (HST-2/HPST-2 made by Fuji) and 30% organic paste base material composed of ethyl cellulose, butyl Carbitol acetate and α-terpineol. Application of the layer by means of screen printing, then traversing a temperature profile up to 1330° C. as shown in FIG. 1.

We claim:

1. A method of producing an inert, catalytically active or gas-sensitive ceramic layer for a gas sensor, comprising:
    (a) a step for coating an uncoated substrate thermally and chemically stable from about 300° to 1200° C., and electrically insulative with respect to a semiconductor material, with a layer of paste having a thickness of 1 to 100 $\mu$m composed of a powdered semiconductor material and an organic paste material; and
    (b) a step for subjecting the coated substrate of step (a) to a three phase thermal treatment consisting of a first heating phase at a temperature of about 150° C., for evaporating liquid components of the organic paste material; a second heating phase at a temperature of about 350° C., for combusting solid components of the organic paste material without residue; and thereafter, a third heating phase at a temperature of about 1,330° C. for adhering the semiconductor material to the substrate.

2. The method according to claim 1, wherein the layer of paste has a thickness between about 1 to 20 $\mu$m.

3. The method of claim 1, wherein said uncoated substrate is coated with said layer of paste by screen printing.

4. The method according to claim 1, wherein said powdered semiconductor material is SrTiO$_3$.

5. A method of producing inert, catalytically active or gas-sensitive ceramic layers for a gas sensor, comprising:
    (a) a step for coating a substrate thermally and chemically stable from about 300° to 1200° C., and electrically insulative with respect to a semiconductor material, said substrate previously coated with a semiconductor material produced by
        (1) a step for coating an uncoated substrate thermally and chemically stable from about 300° to 1200° C., and electrically insulative with respect to a semiconductor material, with a layer of paste having a thickness of 1 to 100 $\mu$m composed of a powdered semiconductor material and an organic paste material; and
        (2) a step for subjecting the coated substrate of step (1) to a three phase thermal treatment consisting of a first heating phase at a temperature of about 150° C., for evaporating liquid components of the organic paste material; a second heating phase at a temperature of about 350° C., for combusting solid components of the organic paste material without residue; and thereafter, a third heating phase at a temperature of about 1,330° C. for adhering the semiconductor material to the substrate; with another layer of paste having a thickness of 1 to 100 $\mu$m composed of a powdered semiconductor material and an organic paste material; and (b) a step for subjecting the coated substrate of step (a) to a three phase thermal treatment consisting of a first heating phase at a temperature of about 150° C., for evaporating liquid components of the organic paste material; a second heating phase at a temperature of about a 350° C., for combusting solid components of the organic paste material without residue; and thereafter, a third heating phase at a temperature of about 1,330° C. for adhering the semiconductor material to the substrate.

6. The method according to claim 5, wherein the layer of paste has a thickness between about 1 and 20 $\mu$m.

7. The method of claim 5, wherein said substrate is coated with said layer of paste by screen printing.

8. The method according to claim 5, wherein said powdered semiconductor material is SrTiO$_3$.

* * * * *